United States Patent
Basheer et al.

(10) Patent No.: US 11,414,623 B2
(45) Date of Patent: Aug. 16, 2022

(54) EFFICIENT BIOMASS CARBON-BASED SOLID ACID ESTERIFICATION CATALYST FOR PRODUCING BIODIESEL

(71) Applicant: KING FAHD UNIVERSITY OF PETROLEUM AND MINERALS, Dhahran (SA)

(72) Inventors: Chanbasha Basheer, Dhahran (SA); Abdulaziz Al-Saadi, Dhahran (SA); Muhammad Azeem Akbar, Dhahran (SA); Rashed Saed Bakdash, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/425,257

(22) Filed: May 29, 2019

(65) Prior Publication Data
US 2020/0377820 A1  Dec. 3, 2020

(51) Int. Cl.
| | | |
|---|---|---|
| *C11C 3/00* | (2006.01) | |
| *B01J 35/10* | (2006.01) | |
| *B01J 21/18* | (2006.01) | |
| *B01J 37/20* | (2006.01) | |
| *B01J 37/34* | (2006.01) | |
| *B01J 37/00* | (2006.01) | |
| *C12P 7/649* | (2022.01) | |

(52) U.S. Cl.
CPC ............... *C11C 3/003* (2013.01); *B01J 21/18* (2013.01); *B01J 35/1009* (2013.01); *B01J 35/1014* (2013.01); *B01J 35/1019* (2013.01); *B01J 37/0036* (2013.01); *B01J 37/20* (2013.01); *B01J 37/346* (2013.01); *C12P 7/649* (2013.01)

(58) Field of Classification Search
CPC ............ C12P 7/649; C12P 7/249; C12P 7/269
See application file for complete search history.

(56) References Cited

U.S. PATENT DOCUMENTS

2012/0066365 A1  3/2012 Ruwwe et al.

FOREIGN PATENT DOCUMENTS

| CN | 101298566 A | 11/2008 |
|---|---|---|
| CN | 101314138 A | 12/2008 |
| CN | 101890364 A | 11/2010 |
| CN | 201289629 B * | 3/2013 |
| CN | 102965203 B * | 6/2014 |
| CN | 103480356 8 | 1/2016 |
| KR | 101264543 B1 * | 2/2013 |

OTHER PUBLICATIONS

Xiaobo Fu, A microalgae residue based carbon solid acid catalyst for biodiesel production, Bioresource Technology, vol. 146, 2013, pp. 767-770.*

(Continued)

*Primary Examiner* — Deborah D Carr
(74) *Attorney, Agent, or Firm* — Oblon, McClelland, Maier & Neustadt, L.L.P.

(57) ABSTRACT

A method for producing biodiesel using a sulfonated, carbonaceous catalyst produced from rice husk, *Moringa* seeds, or algae biomass, a method for producing the catalyst, and the catalyst itself.

9 Claims, 10 Drawing Sheets

(56) References Cited

OTHER PUBLICATIONS

Abdulaziz A. Al-Saadi, et al., "Preparation and characterization of biomass carbon-based solid acid catalysts for the esterification biodiesel from marine algae", 13$^{th}$ International Congress on Biofuels & Bioenergy and Biofuels & Bioeconomy, Journal of Fundamentals of Renewable Energy and Applications, vol. 8, Oct. 18-20, 2018, p. 78.

Danlin Zeng, et al., "Synthesis porous carbon-based solid acid from rice husk for esterification of fatty acids", Microporous and Mesoporous Materials, 2015, 27 pages.

Nurul Hajar Embong, et al., "Preparation of Biodiesel from Palm Oil Decanter Cake with Sulfonating Rice Husk Ash as a Catalyst", ARPN Journal of Engineering and Applied Sciences, vol. 11, No. 11, Jun. 2016, pp. 7225-7228.

Ming Li, et al., "Preparation of solid acid catalyst from rice husk char and its catalytic performance in esterification", Chinese Journal of Catalysis, vol. 34, Issue 9, Sep. 2013, pp. 1674-1682 (Abstract only).

\* cited by examiner

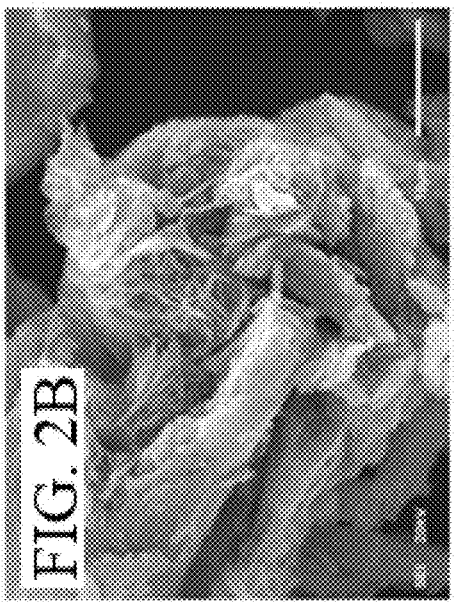
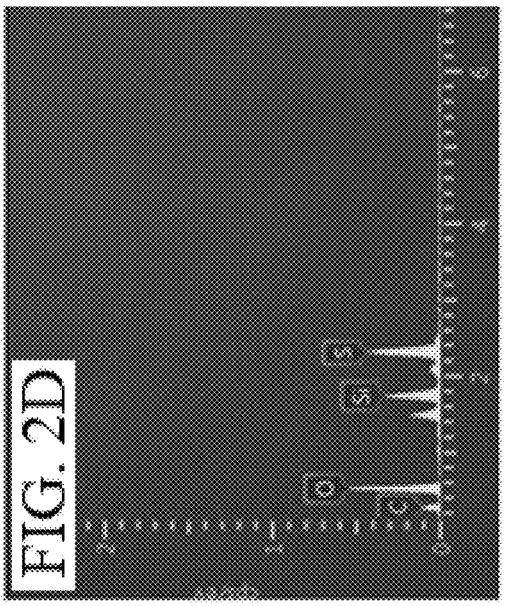
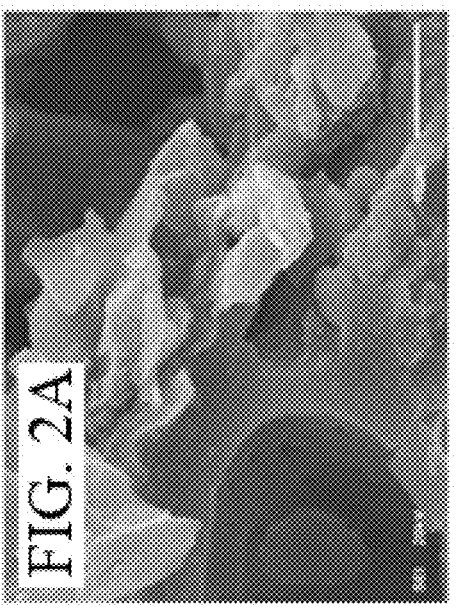

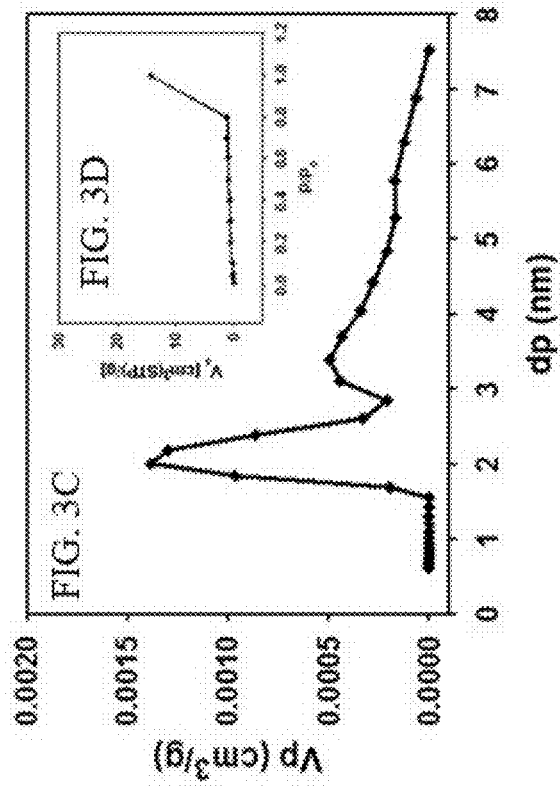
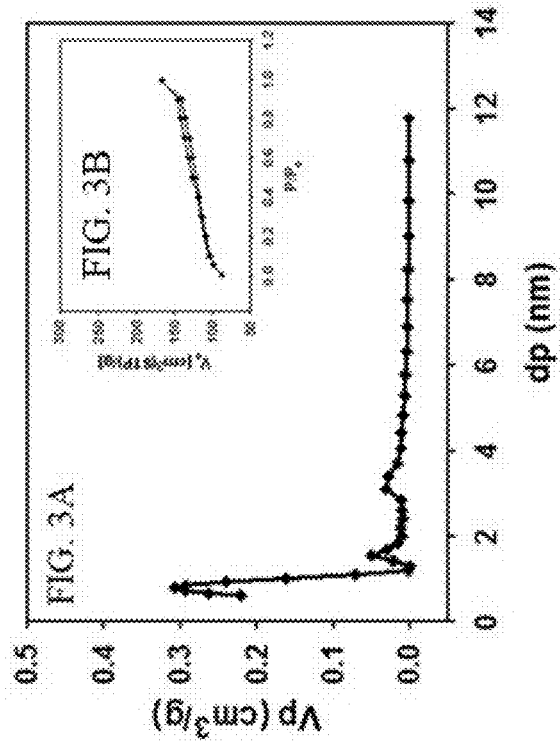
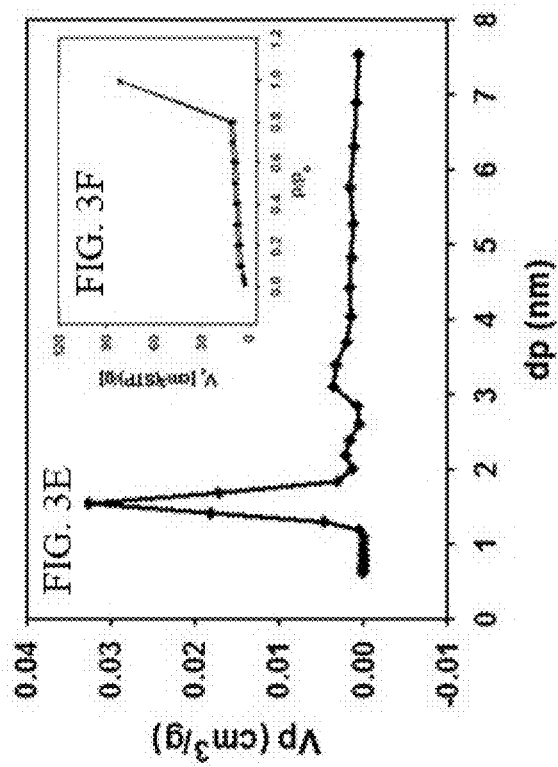

EFFICIENT BIOMASS CARBON-BASED SOLID ACID ESTERIFICATION CATALYST FOR PRODUCING BIODIESEL

STATEMENT OF ACKNOWLEDGEMENT

The authors gratefully acknowledge the funding support of the Deanship of Scientific Research at King Fahd University of Petroleum and Minerals through an undergraduate student project grant No. USRG 1701.

BACKGROUND OF THE INVENTION

Field of the Invention

The invention pertains to the field of chemical catalysts, more specifically to sulfonated carbon-based catalysts made from particular biomass and providing superior performance for esterifying biodiesel.

Background Art

The increase in crude oil demand and limited oil reserves have led to an intense debate about future of petroleum-based fuels and a shift towards alternative energy resources; M. Y. Koh, T. I. Mohd. Ghazi, A review of biodiesel production from *Jatropha curcas* L. oil, Renew. Sustain. Energy Rev. 15 (2011) 2240-2251. doi:10.1016/j.rser.2011.02.013; J. L. Hallock, P. J. Tharakan, C.A.S. Hall, M. Jefferson, W. Wu, Forecasting the limits to the availability and diversity of global conventional oil supply, Energy. 29 (2004) 1673-1696. doi:10.1016/j.energy.2004.04.043. Alternate energy sources such as biodiesel are required to address many financial and environmental issues; T. N. Veziroğlu, S. Şahi'n, 21st Century's energy: Hydrogen energy system, Energy Convers. Manag. 49 (2008) 1820-1831. doi:10.1016/j.enconman.2007.08.015; S. Bilgen, Structure and environmental impact of global energy consumption, Renew. Sustain. Energy Rev. 38 (2014) 890-902. doi:10.1016/j.rser.2014.07.004.

Biodiesel is the unique alternative fuel because its life cycle energy balance is positive, its major features are similar to diesel fuel, and biodiesel is extensively utilized as a substitute energy source for diesel driven engines; K. Malins, V. Kampars, R. Kampare, J. Prilucka, J. Brinks, R. Murnieks, et al., Properties of rapeseed oil fatty acid alkyl esters derived from different alcohols, Fuel. 137 (2014) 28-35. doi:10.1016/J.FUEL.2014.07.091.

Biodiesel can be produced from a variety of raw materials which have a high percentage of fatty acids or glycerides. These materials include soya bean, corn, sunflower, peanut, and palm oil as well as oil from marine algae which can yield nearly 250 times and 31 times more oil respectively compared to soybeans and palm trees; M. J. Ramos, C. M. Fernández, A. Casas, L. Rodriguez, Á. Pérez, Influence of fatty acid composition of raw materials on biodiesel properties, Bioresour. Technol. 100 (2009) 261-268. doi:10.1016/j.biortech.2008.06.039; F. Ma, M. A. Hanna, Biodiesel production: A review, Bioresour. Technol. 70 (1999) 1-15. doi:10.1016/S0960-8524(99)00025-5; S. A. Scott, M. P. Davey, J. S. Dennis, I. Horst, C. J. Howe, D. J. Lea-Smith, et al., Biodiesel from algae: challenges and prospects, Curr. Opin. Biotechnol. 21 (2010) 277-286. doi:10.1016/j.copbio.2010.03.005.

Oil extracted from marine algae is composed of different types of fatty acids and can contain glycolipids, phospholipids, and glycerides; P. Nautiyal, K. A. Subramanian, M. G. Dastidar, Production and characterization of biodiesel from algae, Fuel Process. Technol. 120 (2014) 79-88. doi:10.1016/j.fuproc.2013.12.003; A. Demirbas, M. Fatih Demirbas, Importance of algae oil as a source of biodiesel, Energy Convers. Manag. 52 (2011) 163-170. doi:10.1016/j.enconman.2010.06.055.

Production of biodiesel is simple and uncomplicated. Any oil-bearing entity such as seeds, animal fats, or marine algae can be used to produce biodiesel. Usually, the transesterification of triglycerides present in oil obtained from above-mentioned sources can produce biodiesel in the presence of a basic catalyst. The reactivity of an alkaline catalyst can be greater than the activity of an acid catalyst; I. Reyero, G. Arzamendi, S. Zabala, L. M. Gandía, Kinetics of the NaOH-catalyzed transesterification of sunflower oil with ethanol to produce biodiesel, Fuel Process. Technol. 129 (2015) 147-155. doi:10.1016/j.fuproc.2014.09.008; L. M. Correia, R. M. A. Saboya, N. de Sousa Campelo, J. A. Cecilia, E. Rodríguez-Castellón, C. L. Cavalcante, et al., Characterization of calcium oxide catalysts from natural sources and their application in the transesterification of sunflower oil, Bioresour. Technol. 151 (2014) 207-213. doi:10.1016/j.biortech.2013.10.046; B. Wang, S. Li, S. Tian, R. Feng, Y. Meng, A new solid base catalyst for the transesterification of rapeseed oil to biodiesel with methanol, Fuel. 104 (2013) 698-703. doi:10.1016/j.fuel.2012.08.034; A. Casas, C. M. Fernández, M. J. Ramos, Á. Pérez, J. F. Rodriguez, Optimization of the reaction parameters for fast pseudo single-phase transesterification of sunflower oil, Fuel. 89(2010) 650-658. doi:10.1016/J.FUEL.2009.08.004.

However, basic catalysts exhibit many disadvantages. They increase corrosion of equipment and form unwanted, costly and hard-to-remove soaps by reaction with free fatty acids.

Another route for the transesterification of triglycerides uses sulfuric acid; A. A. Kiss, A. C. Dimian, G. Rothenberg, Solid Acid Catalysts for Biodiesel Production—Towards Sustainable Energy, Adv. Synth. Catal. 348 (2006) 75-81. doi:10.1002/adsc.200505160. However, conventional acid catalysts can form emulsions and soaps during the transesterification of triglycerides. The formation of emulsions and soaps requires further purification and separation of biodiesel that and is costly, time-consuming and produces a large number of waste chemicals; P. M. Ejikeme, I.D. Anyaogu, C. L. Ejikeme, N. P. Nwafor, C. A. C. Egbuonu, K. Ukogu, et al., Catalysis in Biodiesel Production by Transesterification Process—An Insight, E-Journal Chem. 7 (2010) 1120-1132. doi:10.1155/2010/689051; D. Y. C. Leung, X. Wu, M. K. H. Leung, A review on biodiesel production using catalyzed transesterification, Appl. Energy. 87 (2010) 1083-1095. doi:10.1016/j.apenergy.2009.10.006.

In contrast, a solid carbonaceous acid catalyst doesn't require separation and purification once an esterification reaction is complete. Q. Shu, J. Gao, Z. Nawaz, Y. Liao, D. Wang, J. Wang, Synthesis of biodiesel from waste vegetable oil with large amounts of free fatty acids using a carbon-based solid acid catalyst, Appl. Energy. 87 (2010) 2589-2596. doi:10.1016/j.apenergy.2010.03.024.

Direct sulfonation of organic matter involves the carbonization of the material at 400-700° C. and later the carbonaceous matter is sulfonated with sulfuric acid at temperature range of 150-200° C.; H. Yu, S. Niu, C. Lu, J. Li, Y. Yang, Sulfonated coal-based solid acid catalyst synthesis and esterification intensification under ultrasound irradiation, Fuel. 208 (2017) 101-110. doi:10.1016/j.fuel.2017.06.122. The catalytic activity and structure of solid acid catalysts can vary widely depending on the source of the biomass and on the activation method.

Surprisingly, the inventors have found that carbon-based solid acid catalysts from rice husk (rice hull; RH), *Moringa oleifera* seeds (MOR) and biomass of lipid-extracted marine algae (BM) using a microwave-based activation procedure outperform conventional acid esterification or transesterification catalysts. The inventors found that these catalysts had active surface areas and were easy to functionalize as acid catalysts using a green procedure based on a microwave assisted method. The catalysts were found to be reusable at least five times for conversion of the model compounds (dodecanoic acid) five times. Conversion of biodiesel was quantitative and no decrease in performance was observed.

BRIEF DESCRIPTION OF THE INVENTION

Embodiments of the invention include, but are not limited to those described below.

One embodiment of the invention is a method for transesterifying a biodiesel feedstock that includes contacting the feedstock and at least one alcohol with a solid carbonaceous acid catalyst for a time and under conditions sufficient to produce biodiesel, wherein the catalyst comprises sulfonated rice husk (RH), *Moringa oleifera* seeds (MOR) or lipid extracted marine algae (BM); and separating the biodiesel from the solid carbonaceous catalyst and glycerol and/or other reaction byproducts.

In some embodiments, this method further includes pretreating the feedstock to remove water, sulfur, phosphorous, phosphatides, gums, sterols, pigments, metals and/or dirt or other solid particles, such as particles having an average diameter larger than 1, 2, 3, 4, 5 or 6 microns.

The feedstock used in the method disclosed above may comprise oil from bacteria, yeast, fungi, algae, or other microbes, from plants or agricultural wastes, or from animal sources, such as tallow, or from recycled oils, such as oily wastes from restaurants. In one embodiment, the feedstock is oil from one or more types of marine algae.

The alcohol used in the method disclosed above is preferably methanol or ethanol, though other alcohols may be used for transesterification. Alcohols include methanol (e.g., methyl alcohol, wood alcohol, wood naphtha or wood spirits), ethanol, and $C_3$-$C_{12}$ alcohols such as n-propanol, isopropanol, n-butanol, isobutanol, and t-butanol. In a preferred embodiment, the alcohol is methanol.

In some preferred embodiments of the invention the method disclosed herein employs a sulfonated carbonaceous catalyst produced from biomass comprising, consisting essentially of, or consisting of rice husk. More preferably, this catalyst comprises sulfonated biomass of sulfonated biomass of rice husk and has a BET surface area of at least 380 $m^2$/g and an acid site density of greater than 3.5 mmol/g.

In another preferred embodiment, the method disclosed herein uses a catalyst that produced from biomass comprising, consisting essentially of, or consisting of *Moringa oleifera* seeds. More preferably, this catalyst comprises sulfonated biomass of *Moringa oleifera* seeds and has a BET surface area of at least 0.20 $m^2$/g and an acid site density of greater than 3.5 mmol/g.

In another preferred embodiment, the method disclosed herein comprises, consists essentially of, or consists of sulfonated biomass of lipid-extracted marine algae. More preferably, this method comprises use of a catalyst comprising sulfonated biomass of lipid-extracted marine algae that has a BET surface area of at least 10 $m^2$/g and an acid site density of at least 0.24 mmol/g.

In some embodiments, the method disclosed herein will further include separating the biodiesel by removing the solid carbonaceous catalyst, alcohol, glycerol, and/or water.

In some embodiments, the method as disclosed herein comprises a sulfonated carbonaceous catalyst bound to a substrate and the contacting occurs in a fixed bed reactor.

In some embodiments of the method disclosed herein the solid carbonaceous acid catalyst is made by digesting biomass in sulfuric acid at 20, 25, 50, 75, 100, 150, 200, 250, 300 or >300° C. under microwave radiation; drying, milling and/or otherwise pulverizing digested material into a fine powder; and sulfonating the fine powder by mixing it with $SO_3$ fuming $H_2SO_4$ under microwave radiation.

Another embodiment of the invention is directed to a method for making a solid carbonaceous catalyst which includes digesting biomass in sulfuric acid at 20, 25, 50, 75, 100, 150, 200, 250, 300 or >300° C. under microwave radiation; drying, milling and/or otherwise pulverizing digested material into a fine powder, and sulfonating the fine powder by mixing it with $SO_3$ fuming $H_2SO_4$ under microwave radiation; wherein the biomass is selected from the group consisting of at least one of biomass from rice husk, biomass from *Moringa oleifera*, and biomass from marine algae. In an alternative embodiment, biomass for another microbial, plant or animal source may be used. More specifically, the biomass may comprise, consist essentially of, or consist of rice husk; *Moringa oleifera* seeds, or biomass derived from marine algae. The invention as disclosed herein also includes a solid carbonaceous catalyst made by the methods disclosed herein.

Another embodiment of the invention is a solid carbonaceous catalyst per se comprising sulfonated biomass, such as biomass from rice husk, *Moringa oleifera* seeds, or biomass derived from marine algae, or other kinds of biomass.

In some embodiments a catalyst derived from rice husk has a SBET ($m^2$/g) ranging from about 380, 390, 400, 410, 410.871, 420, 430, 440 or 450 and/or a Vp ($cm^3$/g) ranging from 0.17, 0.18, 0.19, 0.20, 0.209, 0.21, 0.22, 0.23 or 0.24 and/or a dp (nm) ranging from 0.75, 0.76, 0.77, 0.78, 0.785, 0.79, 0.80, 0.81 or 0.82 and/or an acid site density ranging from 3.5, 3.75, 4, 4.21, 4.25, 4.75 to 5, and/or a TOF ranging from 2, 2.25, 2.5, 2.73, 2.75, 3, 3.25, to 3.5. In some embodiments this catalyst will be stable and retain catalytic activity at temperatures ranging from 25, 50, 100, 150, 200, 250, 300, 350, 400, 450, 500 or >500° C. The catalyst may be used or reused 1, 2, 3, 4, 5 or more times in an esterification or transesterification. The inventors found that high temperatures above ambient or room temperature were not necessary for quantitative transesterification.

In some embodiments a catalyst derived from *Moringa oleifera* seeds has a SBET ($m^2$/g) ranging from about 2.1, 2.2, 2.3, 2.4, 2.456, 2.5, 2.6, to 2.7 and/or a Vp ($cm^3$/g) ranging from 0.0008, 0.0009, 0.001, 0.002, 0.003, 0.004 or 0.005 and/or a dp (nm) ranging from 1.6, 1.7, 1.8, 1.9, 2.000, 2.1, 2.2, 2.3 or 2.4 and/or an acid site density ranging from 3.5, 3.75, 4.0, 4.1, 4.2, 4.21, 4.25, 4.5, 4.75 to 5, and/or a TOF ranging from 1.0, 1.25, 1.5, 1.70, 1.75, 2, 2.25 to 2.5. In some embodiments this catalyst will be stable and retain catalytic activity at temperatures ranging from 25, 50, 100, 150, 200, 250, 300, 350, 400, 450, 500 or >500° C. The catalyst may be used or reused 1, 2, 3, 4, 5 or more times in an esterification or transesterification.

In some embodiments a sulfonated catalyst derived from marine algae has a SBET ($m^2$/g) ranging from about 10, 12.5, 15, 17.5, 20, 20.046, 22.5, 25, 27.5, to 30 and/or a Vp ($cm^3$/g) ranging from 0.014, 0.015, 0.016, 0.017, 0.018, 0.019, 0.020, 0.021, to 0.022 and/or a dp (nm) ranging from 1.1, 1.2, 1.3, 1.4, 1.5, 1.543, 1.6, 1.7, 1.8 or 1.9 and/or an acid site density ranging from 0.24, 0.25, 0.26, 0.27, 0.28, 0.29 to 0.30, and/or a TOF ranging from 17, 18, 19, 20, 21, 21.29, 22, 23, 24, to 25. The catalyst may be used or reused 1, 2, 3, 4, 5 or more times in an esterification or transesterification.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A. SEM images of sulfonated *Moringa*.

FIG. 2B. SEM images of sulfonated rice husk.

FIG. 2C. SEM images of sulfonated biomass.

FIG. 2D. EDX spectra of sulfonated rice husk.

FIG. 3A. Pore-size distribution of $SO_3H$—RH.

FIG. 3B. Adsorption and desorption isotherm providing the distributions of pore dimensions.

FIG. 3C. Pore-size distribution of $SO_3H$-MOR.

FIG. 3D. Adsorption and desorption isotherm providing the distributions of pore dimensions.

FIG. 3E. Pore-size distribution of $SO_3H$-BM.

FIG. 3F. Adsorption and desorption isotherm providing the distributions of pore dimensions.

DETAILED DESCRIPTION OF THE INVENTION

Figure 1:
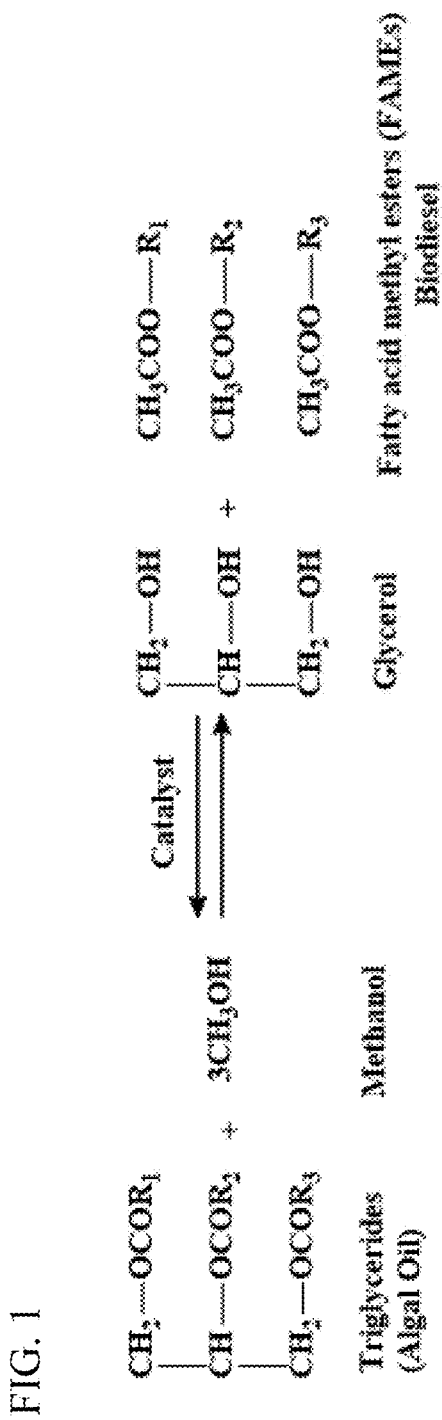
FIG. 1. Biodiesel synthesis by transesterification process from algal oil.

Algae include prokaryotic autotrophic algae and eukaryotic algae, microalgae as well as multicellular algae and macroalgae from marine, brackish water, freshwater, or other aqueous sources such as aqueous medium in an algae culture system. Algae may be classified as brown, green, red, yellow, Golden, green-yellow, blue-green or glaucophytic algae. Algae may express chlorophylls a, b or c and various kinds of pigments. Microalgae or other forms of algae may be those endogenous to waters of a location where biofuel is made or processed, for example, from the waters of biofuel or biodiesel facilities in the Kingdom of Saudi Arabia. Biomass from microalgae and other kinds of algae, preferably those algae producing biodiesel feedstocks, may be used in the invention.

Nonlimiting examples of microalgae that can be used in accordance with the present invention to produce a feedstock or for production of a catalyst are described below. More specifically, algal taxa belonging to the Cyanophyta, including Cyanophyceae, are those being Prokaryotae, which have the ability of oxygen evolution-type photosynthesis and are classified into the following orders and families. Chroococcales include Microcyslaceae, Chroococcaceae, Entophysalidaceae, Chamaesiphoniaceae, Dermocarpellaceae, Xenococcaceae, and Hydrococcaceae, Oscillatoriales includes Borziaceae, Pseudanabaenaceae, Schizotrichaceae, Phormidiaceae, Oscillatoriaceae, and Homoeotrichaceae, Nostocales includes Scytonemataceae, Microchaetaceae, Rivulariaceae, and Nostocaceae, and Stigonematales includes Chlorogloeopsaceae, Capsosiraceae, Stigonemataceae, Fischerellaceae Borzinemataceae, Nostochopsaceae, and Mastigocladaceae.

Chlorophyta include Chlorophyceae, Prasinophyceae, Pedinophyceae, Trebouxiophyceae, and Ulvophyceae. More specifically, Chlorophyceae includes *Acetabularia, Acicularia, Actinochloris, Amphikrikos, Anadyomene, Ankistrodesmus, Ankyra, Aphanochaete, Ascochloris, Asterococcus, Asteromonas, Astrephomene, Atractomorpha, Axilococcus, Axilosphaera, Basichlamys, Basicladia, Binuclearia, Bipedinomonas, Blastophysa, Boergesenia, Boodlea, Borodinella, Borodinellopsis, Botryococcus, Brachiomonas, Bracteacoccus, Bulbochaete, Caespitella, Capsosiphon, Carteria, Centrosphaera, Chaetomorpha, Chaetonema, Chaetopeltis, Chaetophora, Chalmasia, Chamaetrichon, Characiochloris, Characiosiphon, Characium, Chlamydella, Chlamydobotrys, Chlamydocapsa, Chiamydomonas, Chlamydopodium, Chloranomala, Chlorochydridion, Chlorochytrium, Chlorocladus, Chlorocloster, Chlorococcopsis, Chlorococcum, Chlorogonium, Chloromonas, Chlorophysals, Chlorosarcina, Chlorosarcinopsis, Chlorosphaera, Chlorosphaeropsis, Chlorotetraedron, Chlorothecium, Chodatella, Choricystis, Cladophora, Cladophoropsis, Cloniophora, Closteriopsis, Coccobotrys, Coelastrella, Coelastropsis, Coelastrum, Coenochloris, Coleochlamys, Coronastrum, Crucigenia, Crucigeniella, Ctenocladus, Cylindrocapsa, Cylindrocapsopsis, Cylindrocystis, Cymopolia, Cystococcus, Cystomonas, Dactylococcus, Dasycladus, Deasonia, Derbesia, Desmatractum, Desmodesmus, Desmotetra, Diacanthos, Dicellula, Dicloster, Dicranochaete, Dictyochloris, Dictyococcus, Dictyosphaeria, Dictyosphaerium, Didymocystis, Didymogenes, Dilab filum, Dimorphococcus, Diplosphaera, Draparnaldia, Dunaliella, Dysmorphococcus, Echinocoleum, Elakatothrix, Enallax, Entocladia, Entransia, Eremosphaera, Ettlia, Eudorina, fasciculochloris, Fernandinella, Follicularia, Fottea, Franceia, Friedmannia, Fritschiella, Fusola, Geminella, Gloeococcus, Gloeocystis, Gloeodendron, Gloeomonas, Gloeotila, Golenkinia, Gongrosira, Gonium, Graesiella, Granulocystis, Gyorfiana, Haematococcus, Hazenia, Helicodictyon, Hemichloris, Heterochlamydomonas, Heteromastix, Heleroretracystis, Hormidiospora, Hormidium, Hormotila, Hormotilopsis, Hyalococcus, Hyalodiscus, Hyalogonium, Hyaloraphidium, Hydrodictyon, Hypnomonas, Ignatius, Interflum, Kentrosphaera, Keratococcus, Kermatia, Kirchneriella, Koliella, Lagerheimia, Lautosphaeria, Leptosropsis, Lobocystis, Lobomonas, Lola, Macrochloris, Marvania, Micractinium, Microdictyon, Microspora, Monoraphidium, Muriella, Mychonastes, Nanochlorum, Nautococcus, Neglectella, Neochloris, Neodesmus, Neomeris, Neospongiococcum, Nephrochlamys, Nephrocytium, Nephrodiella, Oedocladium, Oedogonium, Oocystella, Oocystis, Oonephris, Ourococcus, Pachycladella, Palmella,*

*Palmellococcus, Palmellopsis, Palmodictyon, Pandorina, Paradoxia, Parietochloris, Pascherina, Paulschuzia, Pectodictyon, Pediastrum, Pedinomonas, Pedinopera, Percursaria, Phacotus, Phaeophila, Physocytium, Pilina, Planctonema, Planktosphaeria, Platydorina, Platymonas, Pleodorina, Pleurastrum, Pleurococcus, Ploeotila, Polyedriopsis, Polyphysa, Polytoma, Polytomella, Prasinocladus, Prasiococcus, Protoderma, Protosiphon, Pseudendocloniopsis, Pseudocharacium, Pseudochlorella, Pseudochlorococcum, Pseudococcomyxa, Pseudodictyosphaerium, Pseudodidvmocystis, Pseudokirchneriella, Pseudopleurococcus, Pseudoschizomeris, Pseudoschroederia, Pseudostichococcus, Pseudotetracystis, Pseudotetradron, Pseudotrebouxia, Pteromonas, Pulchrasphaera, Pyramimonas, Pyrobofrys, Quadrigula, Radiofilum, Radiosphaera, Raphidocelis, Raphidonema, Raphidonemopsis, Rhizoclonium, Rhopalosolen, Saprochaete, Scenedesmus, Schirochlamys, Schizomeris, Schroederia, Schroederiella, Scotiellopsis, Siderocystopsis, Siphonocladus, Sirogonium, Sorastrum, Spermatozopsis, Sphaerella, Sphaerellocystis, Sphaerellopsis, Sphaerocvstis, Sphaeroplea, Spirotaenia, Spongiochloris, Spongiococcum, Stephanoptera Stephanosphaera, Stigeoclonium, Slruvea, Tetmemorus, Tetrabaena, Tetracystis, Tetradesmus, Tetraedron, Tetrallantos, Tetraselmis, Tetraspora, Tetrastrum, Treubaria, Triploceros, Trochiscia, Trochisciopsis, Ulva, Uronema, Valonia, Valoniopsis, Ventricaria, Viridiella, Vitreochlamys, Volvox, Volvulina, Westella, Willea, Wislouchiella, Zoochlorella, Zygnemopsis, Hyalotheca, Chlorella, Pseudopleurococcum and Rhopalocystis,* Prasinophyceae includes *Heteromastix, Mammella, Mantoniella, Micromonas, Nephroselmis, Ostreococcus, Prasinocladus, Prasinococcus, Pseudoscourfielda, Pycnococcus, Pyramimonas, Scherfelia,* Pedinophyceae includes *Marsupiomonas, Pedinomonas, Resultor,* Trebouxiophyceae includes *Apatococcus, Asterochloris, Auxenochlorella, Chlorella, Coccomyxa, Desmococcus, Diclyochloropsis, Elliptochloris, Jaagiella, Leposira, Lobococcus, Makinoella, Microthamnion, Myrmecia, Nannochloris, Oocystis, Prasiola, Prasiolopsis, Prototheca, Stichococcus, Tetrachlorella, Trebouxia, Trichophilus, Watanabea and Myrmecia,* Ulvophyceae includes *Acrochaete, Bryopsis, Cephaleuros, Chlorocyslis, Enteromorpha, Gloeotilopsis, Halochlorococcum, Ostreobium, Pirula, Pithophora, Planophila, Pseudendoclonium, Trentepohlia, Trichosarcina, Ulothrix, Bolbocoleon, Chaetosiphon, Eugomontia, Oltmannsiellopsis, Pringsheimiella, Pseudodendroclonium, Pseudulvella, Sporocladopsis, Urospora,* and *Wittrockiella.*

Rhodophyta include *Acrochaetium, Agardhiella, Antithamnion, Antithamnionella, Asterocyis, Andouinella, Balbiania, Bangia, Batrachospermum, Bonnemaisonia, Bostrychia, Callithamnion, Caloglossa, Ceramium, Champia, Chroodactylon, Chroothece, Compsopogon, Compsopogonopsis, Cumagloia, yanidium, Cystoclonium, Dasya, Digenia, Dixoniella, Erythrocladia, Erythrolobas, Erythrotrichia, Flintiella, Galdieria, Gelidnim, Glaucosphaera, Gomotrichum, Gracilaria, Grateloupia, Grifithsia, Hildenbrandia, Hymenocladiopsis, Hypnea, Laingia, Membranoptera, Myriogramme, Nemalion, Nemnalionopsis, Neoagardhiella, Palmaria, Phyllophora, Polyneura, Polysiphonia, Porphyra, Porphyridium, Pseudochantransia, Pterocladia, Pugetia, Rhodella, Rhodochaete, Rhodochorton, Rhodosorus, Rhodospora, Rhodymenia, Seirospora, Selenastrum, Sirodotia, Solieria, Spermothamnion, Spyridia, Stylonema, Thorea, Trailiella* and *Tuomeya.*

Cryptophyta include Cryptophyceae. More specifically, *Campylomonas, Chilomonas, Chroomonas, Cryptochrysis, Cryptomonas, Goniomonas, Guillardia, Hanusia, Hemiselmis, Plagioselmis, Proteomonas, Pyrenomonas, Rhodomonas* and *Stroreatula.*

Chlorarachniophyta include *Chlorarachnion, Lotharella* and *Chatonella.*

Haptophyla include *Apistonema, Chrysochromulina, Coccolithophora, Corcontochrysis, Cricosphaera, Diacronema, Emiliana, Pavlova, Ruttnera, Cruciplacolithus, Prymnesium, Isochrysis, Calyptrosphaera, Chrysotila, Coccolithus, Dicrateria, Heterosigma, Hymenomonas, Imantonia, Gephyrocapsa, Ochrosphaera, Phaeocystis, Platychrysis, Pseudoisochrysis, Syracosphaera* and *Pleurochrysis.*

Euglenophyta include *stasia, Colacium, Cyclidiopsis, Disigma, Euglena, Eutreptia, Eutreptiella, Gyropaigne, Hyalophacus, Khawkinea Astasia, Lepocinclis, Menoidium, Parmidium, Phacus, Rhabdomonas, Rhabdospira, Tetruetreptia* and *Trachelomonas.*

Heterokontophyta include Bacillariophyceae, Phaeophyceae, Pelagophyceae, Xanthophyceae, Eustigmatophyceae, Syanurophyceae, Phaeothamniophyceae and Raphidophyceae. More specifically, Bacillariophyceae includes *Achnanthes, Amphora, Chaetoceros, Bacillaria, Nitzschia, Navicula,* and *Pinnularia,* Phaeophyceae includes *Ascaseira, Asterocladon, Bodanella, Desmarestia, Dicvocha, Dictyota, Ectocarpus, Halopteris, Heribaudiella, Pleurocladia, Porterinema, Pylaiella, Sorocarpus, Spermatochnus, Sphacelaria* and *Waerniella,* Pelagophyceae includes *Aureococcus, Aureoumbra, Pelagococcus, Pelagomonas, Pulvinaria* and *Sarcinochrysis,* Xanthophyceae includes Chloramoebales, Rhizochioridales, Mischococcales, Tribonematales, and Vaucheriales, Eustigmatophvceae includes *Chloridella, Ellipsoidion, Eustigmatos, Monodopsis, Monodus, Nannochloropsis, Polyedriella, Pseudocharaciopsis, Pseudostaurastrum* and *Vischeria* Syanurophyceae includes *allomonas, Synura* and *Tessellaria,* Phaeothamniophyceae includes haeobotrys and Phacothamnion, Raphidophyceae includes *Olisthodiscus, Vacuolaria* and *Fibrocapsa.*

Diatoms include Bolidophyceae, Coscinodiscophyceae, Dinophyceae and Alveolates, Bolidophyceae include *Bolidomonas, Chrysophyceae, Giraudyopsis, Glossomastix, Chromophyton, Chrysamoeba, Chrysochaete, Chrysodidymus, Chrysolepidomonas, Chrysosaccus, Chrysosphaera, Chrysoxys, Cyclonexis, Dinobrvon, Fpichrysis, Epipyxis, Hibberdia, Lagynion, Lepochromulina, Monas, Monochrysis, Paraphysomonas, Phacoplaca, Phacoschizochlamys, Picophagus, Pleurochrysis, Stichogloea* and *Uroglena,* Coscinodiscophyceae include *Bacteriastrum, Bellerochea, Biddulphia, Brockmanniella, Corethron, Coscinodiscus, Eucampia, Extubocellulus, Guinardia, Helicotheca, Leptocylindrus, Leyanella, Lithodesmium, Melosira, Minidiscus, Odentella, Planktoniella, Porosira, Proboscia, Rhizosolenia, Stellarima, Thalassionema, Bicosoecid, Symbiomonas, Actinocyclus, Amphora, Arcocellulus, Detonula, Diatoma, Ditylum, Fragilariophyceae, Asterionellopsis, Delphineis, Grammatophora, Nanofrustulum, Synedra* and *Tabularia,* Dinophyceae includes *Adenoides, Alexandrium, Amphidinium, Ceralium, Ceralocorys, Coolia, Crypthecodinium, Exuviaella, Gambierdiscus, Gonyaulax, Gymnodinium, Gyrodinium, Heterocapsa, Katodinium, Lingulodinium, Pfiesteria, Polarella, Protoceratium, Pyrocysis, Scrippsiella, Symbiodinium, Thecadinium, Thoracosphaera,* and *Zooxanthella.* Alveolates include *Cystodinium, Glenodinium, Oxyrrhis, Peridinium, Prorocentrum,* and *Woloszynskia.* The terms "algae" or "microalgae" term include isolated as well as mixtures of different types of algae.

Cultivation of microalgae. Microalgae biomass can be produced by known methods including by culture systems such as batch, semi-batch, and continuous systems and by phototropic methods; see Alabi, et al., http://_www.fao.org/uploads/media/0901 _Seed_Science_-_Microalgae_technologies_and_processes_for_biofuelsbioenergy_production_in_British_Colum bia.pdf (last accessed May 10, 2019; incorporated herein by reference). Algae, preferably microalgae, can be grown in an open pond, *Enclosed Photobioreactors, Annular Photobioreactor, Tubular* Photobioreactors or Flat-Panel Photobioreactors: Medipali, et al., Biomed Res Int. 2015; 2015: 519513; doi: 10.1155/2015/519513 (incorporated herein by reference). The growth rates and maximum biomass production of microalgae strains in these culture systems are affected by abiotic (light, temperature, pH, salinity, $O_2$, $CO_2$, nutrient stress, and toxic chemicals), biotic (pathogens and competition by other algae), and operational (shear produced by mixing, dilution rate, depth, harvest frequency, and addition of bicarbonate) factors.

Feedstock. Feedstock for transesterification can be any fatty acid or fatty acid mixture from microbial, fungal, vegetable or animal origin, or used cooking oils (UCO). Typically used vegetable oils originate from rapeseed, sunflower, soy and oil palms. Feedstocks may also be acquired from oils extracted from algae, such as marine algae or from *Moringa oleifera* seeds.

Microalgae can produce up to about 80% dry weight of oils. Preferably, a microalgae strain or mixture of strains that produces at least 20, 25, 30, 35, 40, 45, 50, 55, 60, 65, 70, 75, or 80% dry weight of oil is used to produce oils for conversion into biodiesel according to the invention. Cultivated algae may be recovered and processed to remove oils, hydrocarbons or other valuable components such as β-carotene, astaxanthin, xanthophylls, and phycobiliproteins. These oils and hydrocarbons may be used as biofuel feedstocks, such as diesel feedstock, optionally after further processing to remove contaminants such as solid particles and water. Residual biomass may be recovered processed as disclosed herein to produce a sulfonated carbonaceous catalyst.

The method as disclosed herein may be used to esterify a variety of different free fatty acids to produce fatty acid esters, for example, free fatty acids may be esterified with methanol using the carbonaceous catalysts disclosed herein to produce fatty acid methyl esters ("FAMEs"). Fatty acids include long chains of lipid-carboxylic acid found in fats and oils and in cell membranes as a component of phospholipids and glycolipids. Fatty acids include saturated and unsaturated fatty acids, essential fatty acids (i.e., those not made by the human body), omega 3, 6, 7, and 9 fatty acids, cis-fatty acids and trans fatty acids.

The molecules in biodiesel are primarily FAMEs, usually obtained from vegetable oils by transesterification. They are used to produce detergents and biodiesel. One of the reasons for FAME use in biodiesel instead of free fatty acids is to nullify any corrosion that free fatty acids would cause to the metals of engines, production facilities and so forth. Free fatty acids are only mildly acidic, but in time can cause cumulative corrosion unlike their esters. As an improved quality, FAMEs also usually have about 12-15 units higher cetane number than their unesterified counterparts.

Pretreatment. Depending on the origin of the oils and fats some pretreatment is necessary before processing. Water can be removed as it causes the triglycerides to hydrolyze during base-catalyzed transesterification, producing soapstock instead of biodiesel. Virgin oils are optionally refined, but not to food grade level. In some cases the removal of phospholipids and other plant matter is done by degumming. Recycled oils such as used cooking oil ("UCO") can be purged from impurities such as dirt or charred food prior to their use as feedstocks.

Production of sulfonated carbonaceous catalysts. One aspect of the invention relates to a method for producing a sulfonated carbonaceous catalyst, for example, a catalyst for transesterification. This process generally includes reducing a biomass into particles that are easily carbonized or digested by sulfuric acid, then into particles of a size suitable for efficient sulfonation, sulfonation of the particles under low temperature conditions, and recovery of sulfonated carbonaceous catalyst particles.

Pulverizing or grinding. Biomass, such as rice husk, *Moringa oleifera* seeds, or microalgae may be ground, pulverized, or otherwise broken up into particles that are easily digested by sulfuric acid.

Microwaving. Any pattern or intensity of microwaving consistent with the heating rates, holding temperature, and cooling rate of materials forming a sulfonated carbonaceous catalyst may be used. In some embodiments, substrates are continuously microwaved at an intensity ranging between 1 and 2000 Watts. On other embodiments, substrates may be pulsed with microwaves at a set intensity. In one embodiment, the microwave is an Anton Pear, Microwave Reaction System SOLV, Multiwave PRO having a Magnetron frequency: 2455 MHz and a power output of 1800 W.

In some embodiments, the temperature of the initial digestion of biomass using sulfuric acid ranges from 25, 50, 75, 100, 125, 150, 175, 200, or 225, preferably temperature does not exceed 200° C. It is unnecessary to use higher temperatures to produce the catalyst, such as temperatures above 200. Moreover, in these embodiments, it is unnecessary to use a prolonged carbonization or digestion and this step can be completed in 0.5, 0.75, or 1 hours or less. It is not necessary to prolong this step to more than an hour. It is not necessary to use equipment such as oil baths to complete this step.

In some embodiments, the temperature of sulfonation of digested biomass using sulfuric acid ranges from 25, 50, or 75, preferably sulfonation is conducted at a temperature of about 25-75° C. Thus, it is unnecessary to use higher temperatures to produce the catalyst. Moreover, in these embodiments, it is unnecessary to use a prolonged sulfonation and this step can be completed in about 0.25, 0.75, 0.5 hours or less. It is not necessary to prolong this step to more than an hours. It is not necessary to use equipment such as oil baths to complete this step.

The invention preferably uses microwaves to sulfonate the catalyst substrates (e.g., rice husk) to produce sulfonated catalysts. This process is less complicated and shorter than many other modes of catalyst production; for example, in some embodiments of the invention the sulfonation reaction time is 60, 55, 50, 45, 40, 35, 30, 25 or 20 minutes or less. The catalyst produced by the microwaved based method disclosed herein is highly efficient converting fatty acids in a feedstock to esters in yields of 80, 85, 90, 95, 96, 97, 98, 99 or >99%.

The carbonaceous sulfonated catalysts disclosed herein do not require the presence of other ingredients such as alkali or alkaline earth metals, titanates or low density salt compounds. They may be prepared from natural raw materials and used directly for esterification or transesterification without further activation.

A catalyst derived from rice husk may have an SBET ($m^2/g$) ranging from about 380-450 and/or a Vp ($cm^3/g$) ranging from 0.17-0.24 and/or a dp (nm) ranging from 0.75-0.82 and/or an acid site density ranging from 3.5-5, and/or a TOF ranging from 2-3.5. In preferred embodiments this catalyst will be stable and retain catalytic activity for esterification after heat treatment after 100 C. However, the catalytic efficiency is higher at room temperature. The catalyst may be used or reused 1, 2, 3, 4, 5 or more times in an esterification or transesterification. The above ranges include all intermediate values and subranges.

A catalyst derived from *Moringa oleifera* seeds may have a SBET ($m^2/g$) ranging from about 2.1, 2.2, 2.3, 2.4, 2.456, 2.5, 2.6, to 2.7 and/or a Vp ($cm^3/g$) ranging from 0.0008-0.005 and/or a dp (nm) ranging from 1.6-2.4 and/or an acid site density ranging from 3.5 to 5, and/or a TOF ranging from 1.0 to 2.5. In preferred embodiments this catalyst will be stable and retain catalytic activity for esterification or transesterification at temperatures at 25 C. The catalyst may be used or reused 1, 2, 3, 4, 5 or more times in an esterification or transesterification. The above ranges include all intermediate values and subranges.

A sulfonated catalyst derived from marine algae may have a SBET ($m^2/g$) ranging from about 10 to 30 and/or a Vp ($cm^3/g$) ranging from 0.014 to 0.022 and/or a dp (nm) ranging from 1.1 1.9 and/or an acid site density ranging from 0.24 to 0.30, and/or a TOF ranging from 17 to 25. In preferred embodiments this catalyst will be stable and retain catalytic activity for esterification or transesterification at temperature at 25° C. The catalyst may be used or reused 1, 2, 3, 4, 5 or more times in an esterification or transesterification. The above ranges include all intermediate values and subranges.

Biodiesel. The sulfonated carbonaceous catalysts disclosed herein can be used to produce biodiesel. Biodiesel is a liquid which varies in color—between golden and dark brown-depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. A preferred alkyl ester for use as biodiesel is a methyl ester or ethyl ester. Biodiesel produced by a sulfonated carbonaceous catalyst-based method disclosed herein can be used alone or blended with conventional diesel fuel at any concentration in most modern diesel-engine vehicles. When blended with conventional diesel fuel (petroleum diesel), biodiesel may be present from about 0.1, 0.2, 0.5, 1, 2, 5, 10, 20, 50 to about 99.9 wt. %. Much of the world uses a system known as the "B" factor to state the amount of biodiesel in any fuel mix. For example, fuel containing 20% biodiesel is labeled B20 while pure biodiesel is referred to as B100. Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers. Biodiesel can be used as an additive in formulations of diesel to increase the lubricity of pure Ultra-Low Sulfur Diesel (ULSD) fuel, which is advantageous because it has virtually no sulfur content. Biodiesel has advantageous solvent properties compared to petrodiesel and can be used to break down deposits of residues in the fuel lines of vehicles that have previously been run on petrodiesel.

The common international standard for biodiesel is EN 14214. ASTM D6751 is the most common biodiesel standard referenced in the United States and Canada. Germany uses DIN EN 14214 and the UK requires compliance with BS EN 14214.

Esterification/Transesterification conditions. In some embodiments, a reaction mixture for esterifying or transesterifying an oil or fatty acid, such as a feedstock for biodiesel production, will contain 1, 2, 3, 4, 5, 6, 7, 8, 9, 10 or >10 wt. % based on weight of a mixture of the catalyst and feedstock lipids and a molar ratio of 1:1, 1:2, 1:3, 1:4, 1:5, 1:6, 1:7, 1:8, 1:9 to 10:1 of an alcohol, such as methanol to the lipid feedstock is made. Esterification or transesterification may be performed at any suitable temperature, for example, at a temperature ranging from 0, 10, 20, 30, 40, 50, 60, 70, 80, 90, 100 or >100° C. Preferably, the esterification or transesterification is performed at an ambient temperature, such as at a temperature within the range of 20, 25 to 30° C.

Compared to conventional processes for esterification or transesterification, such as conventional methods of producing biodiesel, the sulfonated carbonaceous catalyst-based method disclosed herein provides advantages such as better control of methanol volatilization, increased safety and reduction in health risks in a laboratory production facility, simpler and safer process steps, less energy consumption, reduction in process times, leading to corresponding reductions in processing costs. For example, in some embodiments esterification of a feedstock such as oil from algae may be completed within 10, 15, 20, 25 or 30 minutes. Moreover, due to the high activity of the sulfonated carbonaceous catalysts disclosed herein, the conversion yields of triglycerides to their corresponding esters can range from 80, 85, 90, 95, 96, 97, 98, 99 or >99, up to 100%.

Examples

Materials. Marine microalgae samples were obtained from the local seafront in Al-Khobar, Abu Ali, Jubail, and KFUPM beach. Only one kind of algae was used throughout the study: *Porphyra umbilicalis*.

Rice husk and *Moringa oleifera* were acquired from a local market.

For the sulfonation of carbon-based catalysts and to get biodiesel product, sulfuric acid ($H_2SO_4$, 95%), ethyl acetate (99.5%) and hexane (65.0%), anhydrous sodium sulfate, were purchased from Cromoline. Methyl alcohol (99.95%), heptane (99.9%), and KBr (99.0%) were bought from J. T. Baker. Food industry FAME mixture as internal standard was obtained from Restek.

Catalyst preparation. Three types of carbonaceous materials (Rice husk, *Moringa* and algae biomass) were sulfonated to obtain a solid acid catalyst.

The biomass materials were ground before sulfonation.

Samples (5 gr each) were stirred in 20 ml of 2 M $H_2SO_4$ in a 100 ml Teflon autoclave heated using an Anton Pear, Microwave Reaction System SOLV, Multiwave PRO to digest the biomasses. The temperatures of each 5 gr sample were ramped for 5 min to 200° C., then held for 30 min at 200° C., and then cooled to 40° C.

Subsequently the sample was dried overnight in the oven at 60° C., followed by hand milling into a fine powder. For sulfonation, the fine powder was then blended with 20 ml of 20% $SO_3$ fuming $H_2SO_4$ in the microwave for 30 min.

After cooling to 40° C., the sample was dried overnight at 150°.

The resultant sulfonated rice husk, sulfonated *Moringa oleifera* seeds, and sulfonate biomass were labeled as $SO_3H$—RH, $SO_3H$-MOR, and $SO_3H$-BM, respectively.

Catalyst Characterization: Surface and crystal structure. Field emission scanning electron microscopy (FE-SEM) (Lyra3 TESCAN) was used to characterize the superficial characteristics of the carbonaceous acid catalysts. To confirm the presence of sulfur on the surface of catalysts EDX scan was also done. The crystal structure of formed catalysts was assessed by using Raman spectroscopy (Horiba dispersive Raman spectrometer) within the range of 50-4000 $cm^{-1}$.

Pore anatomy and BET surface area. Impurities present on the surfaces of solid catalysts were initially removed by heating a 0.2 g sample of each catalyst in a glass tube at 200° C. for two hours under vacuum. Nitrogen adsorption isotherms were obtained from an ASAP 2010 analyzer (Micromeritics, Norcross, Ga., USA). Surface areas of catalysts and pore sizes (mean diameters) were determined using the BET equation and Density Functional Theory (DFT) method; P. I. Ravikovitch, G. L. Haller, A. V. Neimark, Density functional theory model for calculating pore size distributions: pore structure of nanoporous catalysts, Adv. Colloid Interface Sci. 76-77 (1998) 203-226. doi:10.1016/ S0001-8686(98)00047-5 and C. Lastoskie, K. E. Gubbins, N. Quirkefts, Pore Size Distribution Analysis of Microporous Carbons: A Density Functional Theory Approach, J. Phys. Chem. 97 (1993). https://_pubs.acs.org/doi/pdf/ 10.1021/j100120a035 (accessed Feb. 14, 2018), both incorporated by reference.

Acid site density. Ion-exchange titration was applied to quantify the acidic functional group density present on the surfaces of sulfonated catalysts. A 0.15 g catalyst sample and 20 ml of 0.5 M NaCl solution were added and mixed in a flask. Ultrasonic mixing for 24 h was done to facilitate the ion-exchange reaction of H ion from —$SO_3H$ group of catalyst with $Na^+$ ion from NaCl. The long contact time of catalyst and NaCl solution resulted in an equilibrium of H* concentration in the supernatant solution. Afterwards, the filtrate solution was titrated against a standardized 0.1 M NaOH solution to detect the endpoints of the reactions. Phenolphthalein was utilized as an indicator. The precise acid site density was determined by using Equation 1:

$$c(H^+) = \frac{c(OH^-) \times \Delta V}{m} \quad (1)$$

In Equation (1), $c(H^+)$ signifies acid site density of a catalyst under study; $c(OH^-)$ denotes sodium hydroxide concentration; $\Delta V$ represents sodium hydroxide quantity used in titration, and m symbolizes the amount of sulfonated catalyst added in the flask for ion exchange reaction.

X-ray diffraction (XRD). Powder diffractograms of $SO_3H$—RH, $SO_3H$-MOR and $SO_3H$-BM catalysts were obtained from Rigaku Miniflex II desktop X-ray diffractometer (tube output voltage 30 kV) at a scan rate of 2.5° $min^{-1}$ from 10 to 70°.

Fourier transform infrared spectroscopy (FTIR). The FTIR spectra were obtained by using a Nicolet 6700 FT-IR (Thermo Electron Corporation) Fourier transform infrared spectroscopy (FTIR). KBR was used to convert sample into pellet, and the spectrum was acquired with resolution of 4 $cm^{-1}$ by the assemblage of 32 scans within the range of 4000-400 $cm^{-1}$.

TGA of catalysts. Thermogravimetric analyses of the catalysts were carried out by heating the catalytic materials at increment frequency of 10° C./min with flow of nitrogen (75 ml/min) up to 1000° C. using a SDT Q 600, TA Instruments, New Castle, Del. The decrease in weight of solid acid catalysts was determined and used to measure the stability of the solid carbonaceous samples.

Collection and processing of algae. Samples of marine red algae (*Porphyra umbilicalis*) were collected from the seafront in AI-Khobar, Abu Ali, Jubail and King Fahd University beach (Half-moon Bay, Khobar). The algae samples were stranded with the help of a grinder to a feasible extent. The pulverized algae materials were desiccated in an incubator for discharging water.

Algae available in the open ocean from eastern province of Saudi Arabia (Dammam, Dhahran and Jubail areas were collected and utilized.

A mixture of solvents—hexane 150 ml and ether 150 ml—was mingled with the 30 g dried crushed algae for the oil extraction. Subsequently, the blend was held at ambient temperature for 5 h for subsiding.

The algal biomass was separated from blend by vacuum filtration, washed with solvent mixture to remove any remains of algal oil left.

The extracted algal oil was kept under vacuum in rotary evaporator in order to eliminate the solvent mixture (hexane and ether).

The mass of solid biomass residues was measured.

Catalytic activity assessment: Procedure for acid-catalyzed esterification. A mixture of catalyst with methanol was produced by blending 0.5 g solid acid catalyst with 2.5 ml methanol with continuously stirring for 30 min.

With the aim of achieving the esterification process, the mixture of catalyst with methyl alcohol was added into a conical flask containing an extracted lipid sample (2.5 ml) and agitated using a magnetic stir bar. A rapid esterification was achieved within 20 min, but the reaction was monitored for a total of 2 hours.

The resulting solution containing biodiesel and sediment was allowed to settle at room temperature and distinct layers of biodiesel and sediment were observed. Samples were centrifuged at 1500 rpm to further isolate biodiesel form sediments and the amount of sediment (glycerin, pigments, etc.) was quantified.

The produced biodiesel was then measured by gas chromatography-mass spectrometry (GC-MS).

The performance of the solid acid catalyst under study was compared with that of sulfuric acid which was employed as homogeneous liquid catalyst. FIG. 1 depicts the basis reaction scheme for producing biodiesel from algal oil.

Turn over frequency (TOF) measurement. Turnover frequencies, TOF [$min^{-1}$] were measured by the consumption of myristic acid and used to assess the capability and activity of the various catalysts. TOF is assessed in relation to myristic acid ($C_{14}H_{28}O_2$) conversion by number of moles of the acid site to its ester ($C_{51}H_{30}O_2$); see Equation 2.

$$C_{14}H_{28}O_2 + CH_3H \rightarrow C_{15}H_{30}O_2 + H_2O \quad (2)$$

As shown by Equation (2) one mole of myristic acid produces the same number of moles of methyl myristate. The TOF calculation for the esterification reaction of myristic acid was done by studying the formation rate of methyl myristate under an initial reaction rate within 10 min. TOFs can be described in Equation (3):

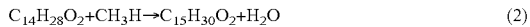

$$TOF = M_D / \tau M_{CAT} \quad (3)$$

where $M_D$ denotes the moles of ester obtained in the reaction time, $\tau$, and $M_{CAT}$ represents the moles of the acid sites obtained from ion-exchange titration procedure. To determine the TOF, a 10 min reaction time was selected for the reaction under study.

Catalyst Sustainability. In order to assess the recycling characteristics of the carbonaceous biomass solid acid catalysts, the reaction of algal oil to produce esters was replicated three times. Once the esterification process was done, a vacuum filtration flask was utilized to isolate catalyst from the reaction mixture which was then dried at ambient condition. After that, the desiccated material was again used in the esterification of the next batch. To carry out the esterification of each batch, a fresh solution carrying same concentration of algal oil and $CH_3OH$ as they were present in the first batch.

Gas chromatography-mass spectrometry (GC-MS). The biodiesel production was assessed by its quantity compared to (i) algal oil present in the algal biomass and (ii) the amount of algal biomass. The mixture of fatty acid methyl ester ("FAME") present in the produced biodiesel was investigated using GC-MS. A 1.0 µL sample was directly injected and analyzed by a Shimadzu 2010 GCMS-QP 2010 Ultra system (Shimadzu Scientific Instruments, Japan) that was outfitted with a mass spectrometer (MS) as a detector and a Rxi-5 Sil MS column (30 m-0.25 mm-0.25 µm) at 200° C. The fatty acids were identified by using Restek Fatty acid mixture a separate standard addition calibration was constructed for each sample collected from the field and the catalyst.

Biodiesel yield % was determined using the following equations.

% Volume Yield=(volume of product/volume of oil fed)×100     Eq. (4)

% Biodiesel yield=FAMEs percentage from GC analysis×% Volume yield     Eq. (5)

The GC-MS analyses gave the distribution of each component produced from the sample.

Microscopic observation and pore anatomy. FIGS. 2A, 2B, and 2C depict SEM micrographs of the $SO_3H$-MOR, $SO_3H$—RH, and $SO_3H$-BM catalysts, respectively. These figures clearly show that the synthesized catalysts had uneven areas holding numerous irregular-shaped particles and macro-pores. Cracks, crevices and some crystals of various sizes in large holes can be observed from the micrographs of the external surface of the $SO_3H$-MOR (FIG. 2A) and $SO_3H$—RH (FIG. 2B). However, in case of $SO_3H$-BM (FIG. 2C), the surface was etched to be rough. The textural properties of $SO_3H$—RH material confirm the presence of a larger surface area. Consequently, the surface of $SO_3H$—RH displayed higher capability to attach the —$SO_3H$ groups and provide active sites for conversion of free fatty acids ("FFAs") to biodiesel.

In FIG. 2D, EDX spectra of $SO_3H$—RH are shown, which confirmed the presence of sulfur, oxygen, and silica accompanied by carbon on the surface. The EDX map of the other catalysts also confirmed the presence of sulfur well distributed on the surface of all carbonized materials along with carbon and oxygen on the surface.

In order to get the more information about the carbonized materials, porosity was examined using the BET method, as shown by FIGS. 3A-3C. The adsorption and desorption isotherm appear in the inset and provide the distributions of pore dimensions. The surface area, obtained from $N_2$ adsorption, pore diameter, and pore volume of sulfonated rice husk, sulfonated *Moringa*, and sulfonated biomass is summarized in Table 1.

TABLE 1

BET surface area (SBET), pore volume ($V_p$), and pore diameter ($d_p$) of the various carbon-based solid acid catalysis.

| Sample | $S_{BET}$ (m²/g) | $V_p$ (cm³/g) | $d_p$ (nm) |
|---|---|---|---|
| Sulfonated RH | 410.871 | 0.209 | 0.785 |
| Sulfonated *Moringa* | 2.456 | 0.002 | 2.000 |
| Sulfonated biomass | 20.046 | 0.018 | 1.543 |

The $SO_3H$—RH, $SO_3H$-MOR, and $SO_3H$-BM display micro-porosity with a pore size of 0.785 nm, 2.000 nm, and 1.543 nm respectively. Out of above mentioned sulfonated catalysts MOR displayed lowest surface area, on the other hand, the $SO_3H$—RH with smallest pore diameter displays highest surface area i.e. 410.871 m²/g. The outcomes indicate that microwave sulfonation promoted the porosity in the raw rice husk as compared to other carbonized catalysts. The smaller surface area or pore volume of the $SO_3H$-MOR and $SO_3H$-BM can be attributed to the collapse of carbon-based structure and very small number of apertures on the surface of these materials can be perceived as in SEM images FIG. 2. Finally, the outcomes revealed that sulfonated rice husk showed the highest surface area and pore volume as compared to the other two materials; see FIGS. 3A-3F.

Figure 4:
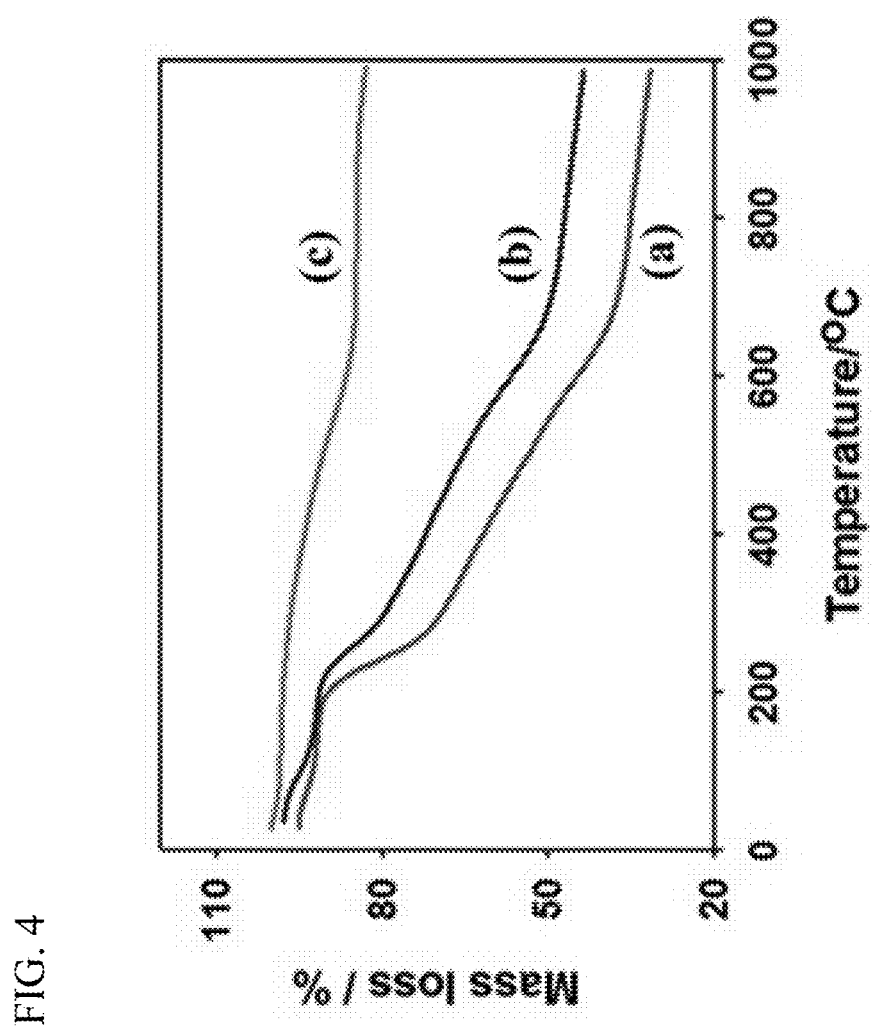
FIG. 4. Thermogravimetric analysis spectra of (a) $SO_3H$-MOR (b) $SO_3H$—RH, and (c) $SO_3H$-BM.

Thermogravimetric analysis. The stability of the carbonaceous acid catalysts was established with TGA analysis (FIGS. 4A-4C). When the temperature reached 1000° C., 27.2% of $SO_3H$-MOR (FIG. 4A), 40.8% of the $SO_3H$—RH (FIG. 4B) and 78.5% of the $SO_3H$-BM (4 FIG. 4C) materials were existent as the residual solid. These outcomes revealed that $SO_3H$-BM catalyst was more stable as compared to $SO_3H$-MOR and $SO_3H$—RH. Three phases in the TGA curves of samples degradation were evaluated. First, the sulfonated catalyst materials displayed a minor decrease in weight at 50-200° C. due to release of physically adsorbed water content in the catalysts, which is primarily due to the hydrophilic nature of —$SO_3H$ groups attached to carbon surface.

Further, an increase in temperature displayed a prominent reduction in weight of $SO_3H$-MOR and $SO_3H$—RH materials which was referred to decomposition of —COOH groups, removal of —OH and sulfur groups in the material.

Last, the mass losses appeared around 600° C. that is due to collapse of the macromolecules and elimination of organic matter.

Figure 5:
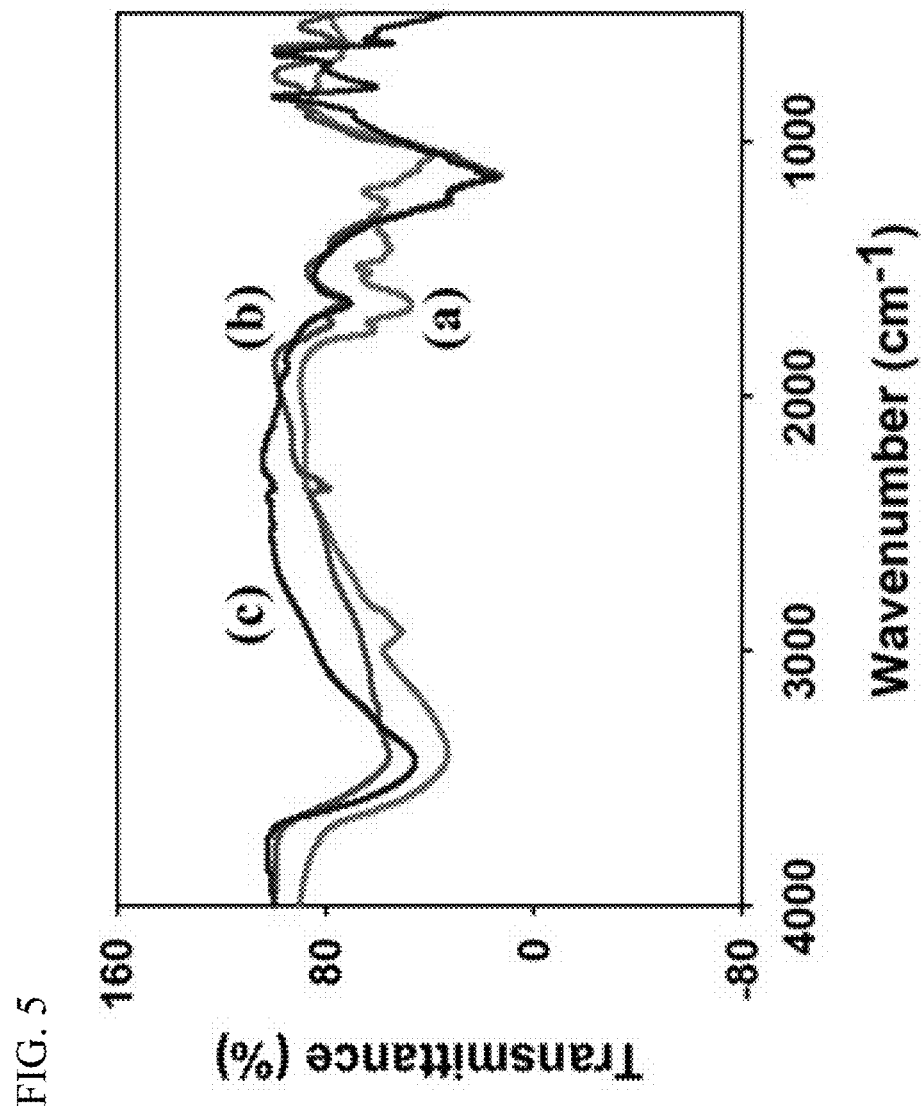
FIG. 5. FT-IR spectra of (a) $SO_3H$-MOR (b) $SO_3H$—RH, and (c) $SO_3H$-BM.

Spectroscopic characterization. FTIR spectra of the carbonaceous catalysts are presented in the FIG. 5. The absorption bands appeared at 1036 cm⁻¹ is attributed to —$SO_2$ Symmetrical stretching mode and 1162 cm⁻¹ accredited to —$SO_2$ asymmetrical stretching mode that verified the existence of —$SO_3H$ group. The stretching bands at 1620 cm⁻¹ indicated the presence of polycyclic compounds. The absorption bands detected at 1743 cm⁻¹ were accredited to the carboxylic group C=O stretching. The bonds that were found in FTIR spectra of the carbon based catalysts established the existence of the —$SO_3H$ groups in the catalyst structure.

Figure 6:
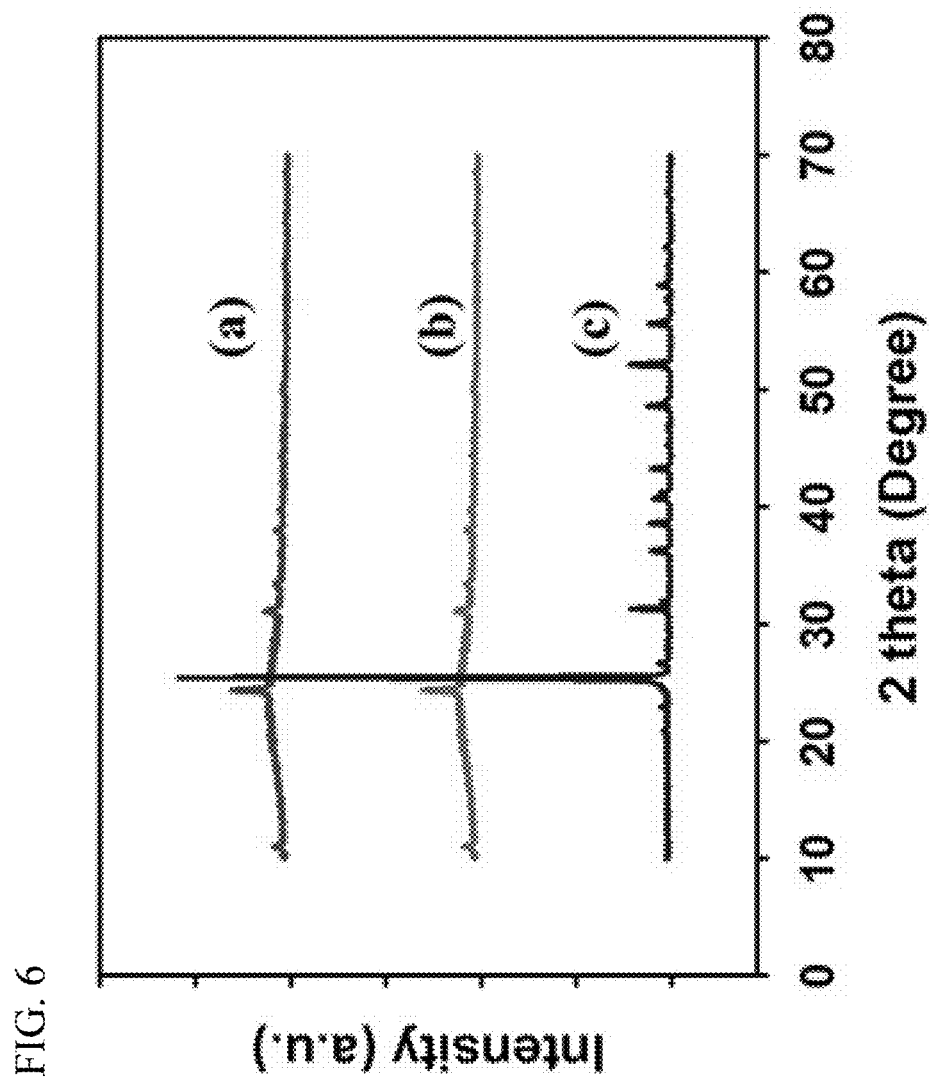
FIG. 6. XRD spectra of carbon-based catalysts, (a) $SO_3H$—RH, (b) $SO_3H$-MOR, and (c) $SO_3H$-BM.

FIG. 6 displays X-ray diffraction (XRD) patterns of different materials sulfonated under similar conditions. A sharp peak appeared around 2θ=25° that is relatively of high intensity in case of $SO_3H$-BM material. This peak is characteristic of unordered carbon materials contain aromatic carbon sheets pointed in an arbitrary manner. This structure is far from any order and thus favorable for attaching the —$SO_3H$ groups. There is a good chance of attachment of —SO$_3$H group to the carbon-based materials resulting in higher catalytic activity. Relatively weak peaks between 2θ=30°-60° are ascribed to the graphite-like structure.

Figure 7:
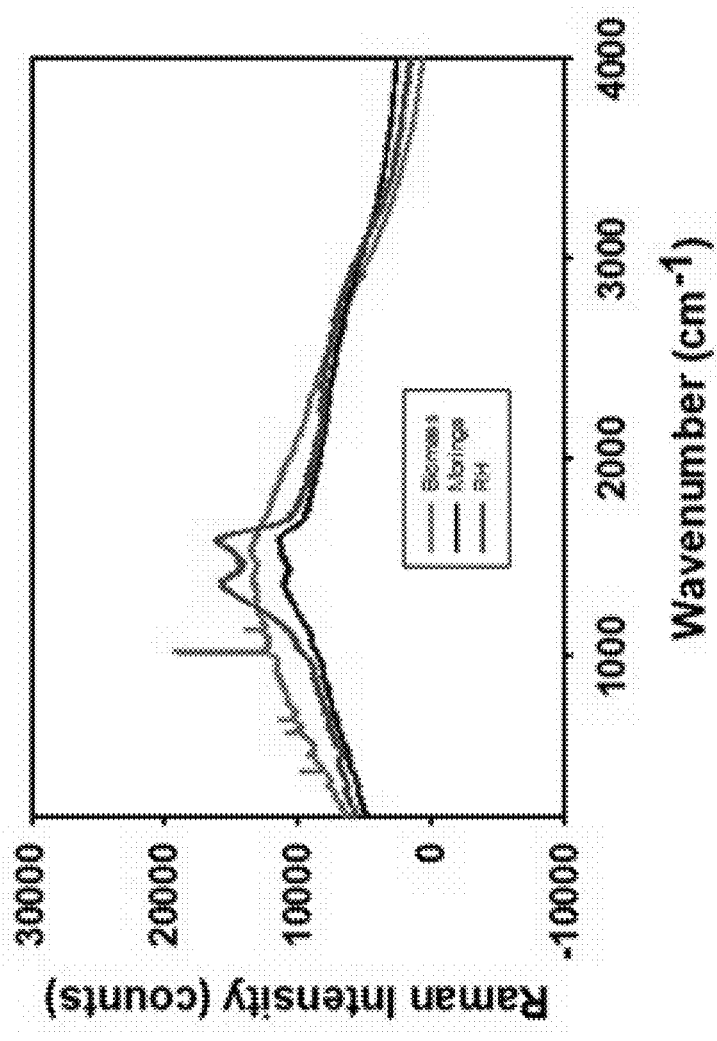
FIG. 7. Raman spectra of carbon-based catalysts, $SO_3H$—RH, $SO_3H$-MOR, and $SO_3H$-BM.

Raman spectrum for the sulfonated carbonaceous catalysts (FIG. 7) displays strong peaks at 1400 cm$^{-1}$ (D-band related to flaws in the graphite layer) and 1586 cm$^{-1}$ (G-band arise on account of vibrations of two adjacent carbon atoms in a single crystal graphite sheet).

Acid site density. For the catalysis of an esterification reaction, the —SO$_3$H groups play and important role. The quantity of —SO$_3$H groups was estimated straightaway by determining the acid site density based on weight presuming that all acidic sites gave rise by H$_2$SO$_4$ treatment were —SO$_3$H groups and reachable. Results from ion-exchange titration are summarized by Table 2.

TABLE 2

Acid site density and TOF of solid catalysts determined by Equation (2) for liquid phase esterification of myristic acid with methanol.

| Catalysts | Acid site density (mmol/g) | TOF (min$^{-1}$) |
| --- | --- | --- |
| SO$_3$H-MOR | 4.21 | 1.70 |
| SO$_3$H-RH | 4.24 | 2.73 |
| SO$_3$H-BM | 0.27 | 21.29 |

The outcomes revealed that SO$_3$H—RH displayed prominently higher acid density as compared to SO$_3$H-MOR and SO$_3$H-BM. These outcomes are in correspondence with the BET data mentioned in Table 1. Where SO$_3$H—RH display relatively higher surface area as compared to other sulfonated catalysts. The arrangement of-of acid site density of carbonaceous materials in decreasing order can be shown as SO$_3$H—RH>SO$_3$H-MOR>SO$_3$H-BM signifying that rice husk is responding the microwave sulfonation in a positive way to give the solid acid catalyst. Algal biomass has lesser sites for binding the —SO$_3$H group on its surface, as a result, the acid site density obtained was 0.40 mmol/g.

Figure 8:
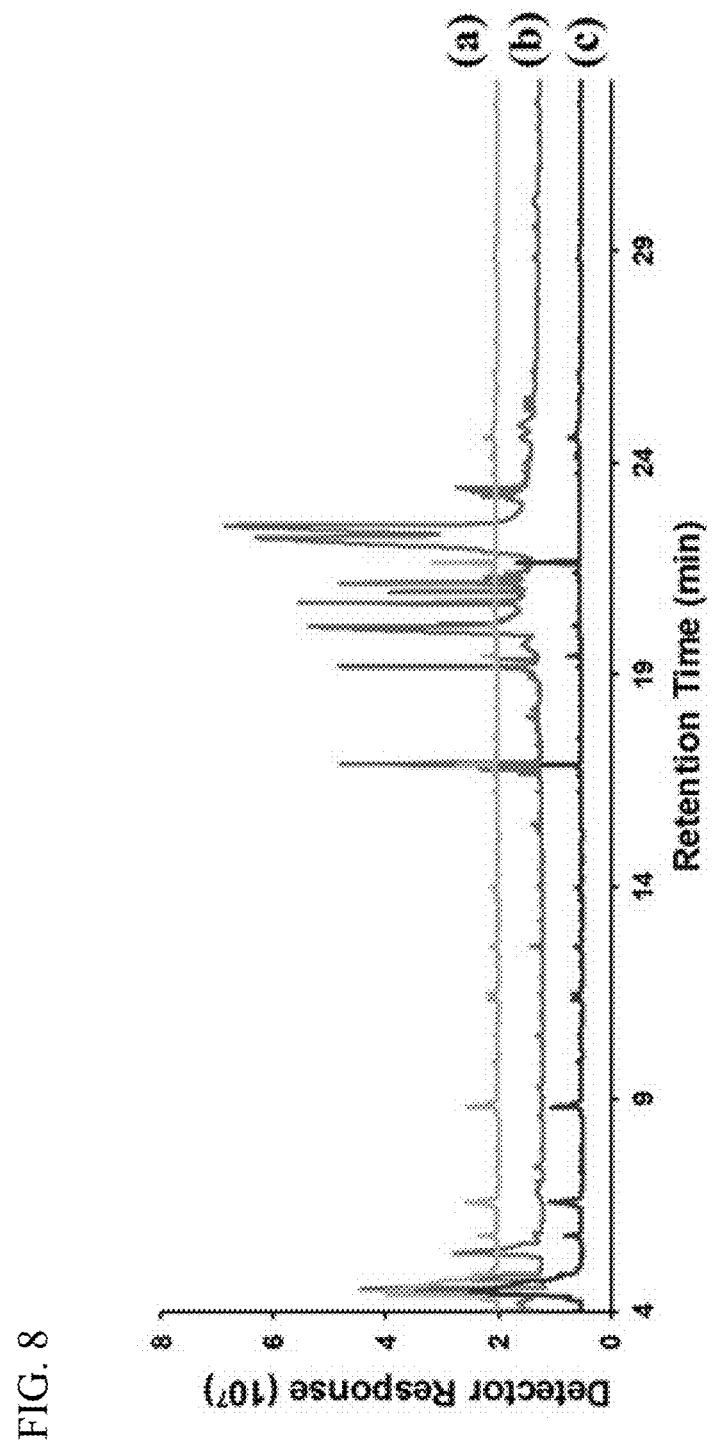
FIG. 8. Gas chromatography-mass spectrometry of biodiesel produced from algae from different locations (a) KFUPM beach, (b) Al-Khobar Cornish, and (c) Abu Ali beach Jubail.

Catalyst activity on Algal oils. To investigate the characteristics of biodiesel GC-MS was used. FIG. 8 illustrates the chromatograms of lipid contents from the algae collected from different areas of the eastern province of Saudi Arabia: (a) KFUPM beach, (b) Al-Khobar Cornish, and (c) Abu Ali beach Jubail. The GC-MS study revealed that the algae collected from the Al-Khobar Cornish have a higher content of lipids as compared to the other two areas. For further optimization of esterification procedure, the algae sample collected form Al-Khobar Cornish was utilized.

The algal oil obtained after extraction was treated with solid acid catalysts derived from *Moringa oleifera* seeds, rice husk, and algal biomass. The catalytic activity of SO$_3$H—RH, SO$_3$H-MOR, and SO$_3$H-BM was compared with sulfuric acid, a well-known catalyst for production of biodiesel.

Figure 9:
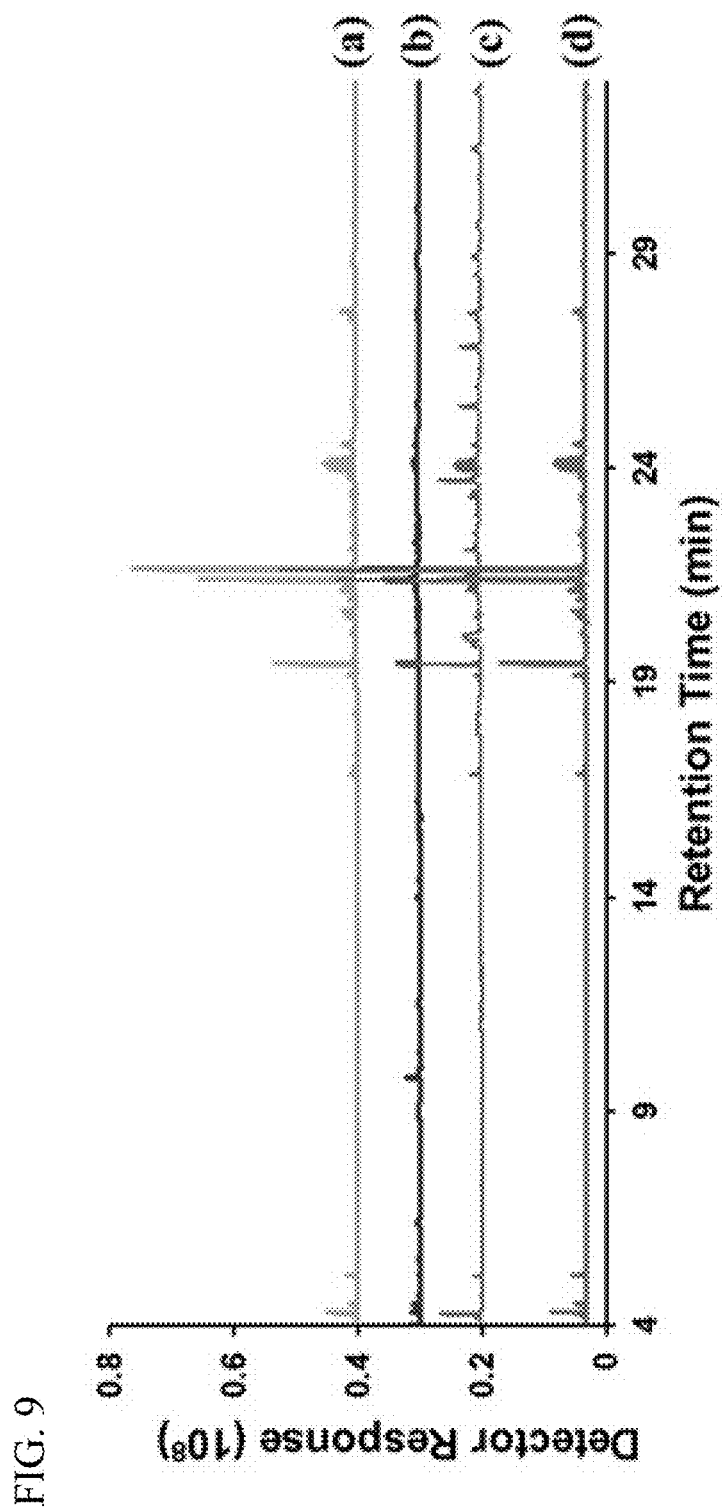
FIG. 9. GC-MS of biodiesel produced from algae from different acid catalysts (a) $SO_3H$—RH, (b)$SO_3H$-MOR, (c) $H_2SO_4$, and (d) $SO_3H$-BM.

There were three characteristic GC-MS chromatograms of FAMEs after esterification procedure. The three peaks recognized FAMEs as tetradecanoic acid methyl ester (C14:1), 9-hexadecanoic acid methyl ester (C17:1) and n-Pentadecanoic acid methyl ester (C16:1). The distinguished FAMEs were substantiated by retention time data and mass fragmentation pattern from earlier studies. In FIG. 9 characteristic glycerol peaks appeared at 4.7-minute retention time in biodiesels from all catalysts due to the existance of excess methyl alcohol to oil ratio of the moles in the extracted algal oil.

The composition of the produced biodiesel slightly varies by changing the nature of the catalyst, however, the three FAME peaks remain there in case of all four catalysts and the calculation of biodiesel % yield was done by considering three FAME peaks. The GC-MS chromatogram (FIG. 8) displays different % yield for the tetradecanoic acid methyl ester (C14:1), 9-hexadecanoic acid methyl ester (C17:1) and n-Pentadecanoic acid methyl ester (C16:1). % yield from sulfonated *Moringa* catalyst is (96%) lowest as compared to sulfonated rice husk (99.8%) and sulfonated biomass (99.9%). Sulfonated rice husk displays the highest yield of 9-hexadecanoic acid methyl ester (C17:1), whereas sulfonated biomass gives the best yield for tetradecanoic acid methyl ester (C14:1) and n-Pentadecanoic acid methyl ester (C16:1).

The % conversion yield of triglycerides to the similar esters was obtained from the GC-MS analysis of the optimum produced biodiesel. The % yield was computed was close to 100%. The TOFs of the produced carbonaceous acid catalysts are revealed in Table 2. It would be distinguished that the TOFs of SO$_3$H-MOR, SO$_3$H—RH, and SO$_3$H-BM are very different from each other. The TOF of SO$_3$H-MOR was inferior comparative to the other biomass based solid catalysts. Hydrophobicity of the catalysts around the acid sites permits the catalyst to achieve greater catalytic activity and plays an important function in achieving greater TOF of the carbonaceous catalysts. H$_2$O is produced during the esterification reaction of myristic acid with methyl alcohol, see Eq. (1). H$_2$O has a capacity to deactivate the H$_2$SO$_4$ that catalyzes the esterification of acetic acid in the presence of methanol due to formation of strong shell around the protons. Consequently, the acetic acid finds it difficult to interact with H$_2$SO$_4$ catalyst. A similar kind of interaction occurs in case of myristic acid, as like acetic acid it is a type of carboxylic acid. Thus, it is likely that the hydrophobic behavior around the acid sites in biomass-based catalysts improves the catalytic action for the esterification of myristic acid. Although, the TOF value for the algal biomass catalyst is highest, its acid site density is very low, so it may may become irrelevant in the context of higher catalytic activity. To summarize, the TOF fallouts, SO$_3$H—RH carry greater acid site density and higher TOF as compared to other catalysts, consequently, it displayed the maximum catalytic action for the esterification process as is apparent from FIG. 8.

Figure 10:
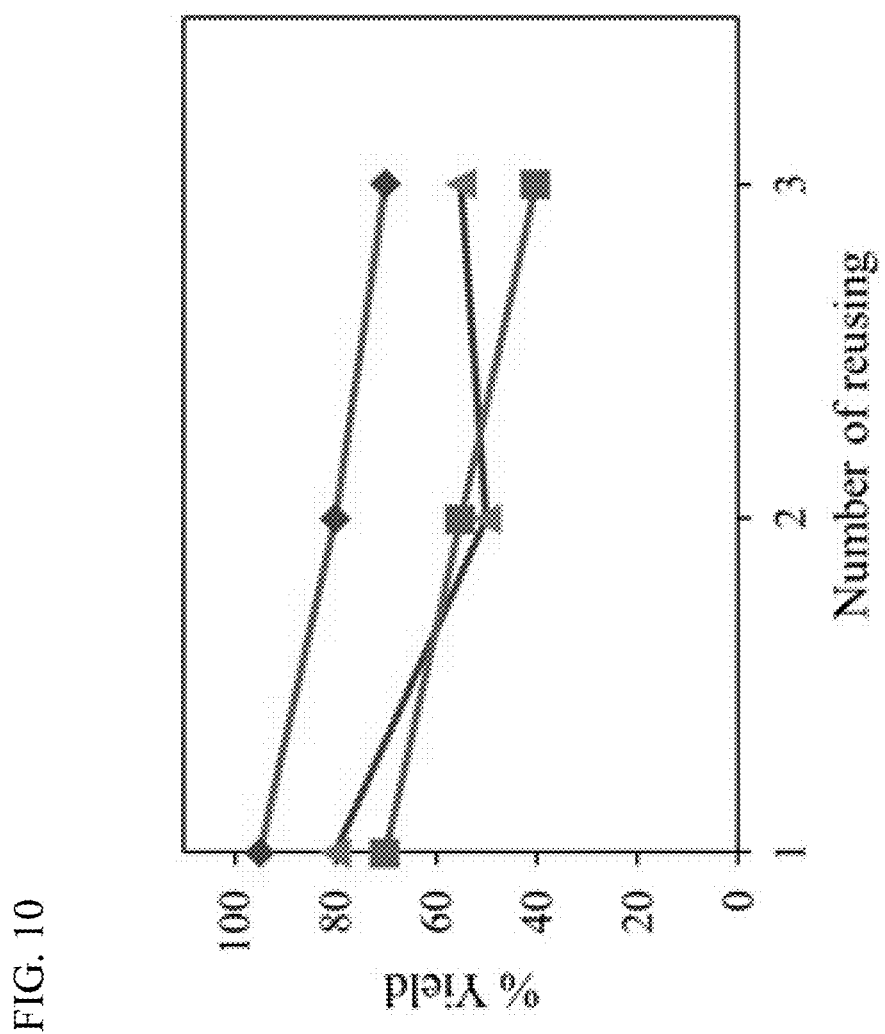
FIG. 10. Reusability of three solid catalysts for repeated batches of esterification of algal oil with methanol. (Reaction conditions: weight of catalyst, palmitic acid, and methanol=0.15, 0.15, and 5 g; temperature=64° C.; reaction time to obtain yield in each batch=5 h.)

Catalyst reusability. A benefit of applying heterogeneous catalysts for a reaction over homogeneous catalysts is the ease of separation of heterogeneous solid catalysts from the reaction mixture. Afterwards they can they can be restored for reprocessing and reuse. The reusability of all the solid acid catalysts was inspected by retrieving the carbon-based catalysts utilized in reaction for 5 h. FIG. 10 shows the consequences for three sequential esterification reactions of algal lipids. As apparent from this figure the reaction capability of all the carbon-based catalyst continuously decreased with the passage of time. The reduction in reaction capability of catalyst can be attributed to the fact that the active sites of the catalysts cannot be triggered to the same number as present in catalysts during first use. Because of catalytic activity of SO$_3$H—RH was less effective over the passage of time and % yield remained higher as compared to SO$_3$H-MOR and SO$_3$H-BM, so SO$_3$H—RH may be the best material to utilize for the esterification of algal oil.

As shown herein, the inventors compared three biomass carbonaceous solid-acid catalysts prepared by controlled microwave sulfonation conditions from the biomass of rice husk (RH), *Moringa oleifera* seeds (MOR) or lipid extracted marine algae (BM). The catalytic performances of all three catalysts were comparable and better than a classical sulfuric acid catalyst. These catalysts efficiently produced fatty acid methyl esters ("FAMES"), including C14 to C17 methyl esters, at almost 100% conversion output. Moreover, these catalysts were reusable.

Biomass carbon-based heterogeneous acid catalysts were formed by sulfonation of rice husk (RH), *Moringa oleifera* seeds (MOR) and biomass of lipid extracted marine algae (BM) in a microwave reactor at 200° C. The physiochemical characteristics of the prepared biomass derived catalysts were determined with Fourier transform infrared spectroscopy, Raman spectroscopy, scanning electron microscopy and X-ray diffraction techniques. These studies confirmed the presence of sulfur-incorporated functional groups on the carbonaceous materials. The acid site density of the catalysts was measured by utilizing ion exchange titration. It was found that $SO_3H$—RH based catalyst carries the most prominent acid site density (4.24 mmol/g by NaOH titration) when compared to other prepared solid-acid catalysts. However, by employing $SO_3H$—RH and $SO_3H$-BM almost full quantitative yield of ester was achieved with a 5 wt. % mixture of catalyst/lipid for reaction time of 20 minutes at a 5:1 M ratio of methyl alcohol/lipid extract, whereas the conventional sulfuric acid catalyst gave 70% yield after 2 hours under the same reaction condition. The results clearly proved that the $SO_3H$—RH displays better catalytic activity and stability when used compared to $SO_3H$-MOR, $SO_3H$-BM and sulfuric acid catalyst.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0,>0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over" "upper" "in front of" or "behind" and the like, may be used herein for ease of description to describe one element or feature's relationship to another element(s)

or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for esterifying a biodiesel feedstock to produce biodiesel, comprising:
    contacting the biodiesel feedstock and at least one alcohol with a solid carbonaceous acid catalyst for a time and under conditions sufficient to produce biodiesel and glycerol,
    wherein the solid carbonaceous acid catalyst comprises carbonized and sulfonated *Moringa oleifera* seeds (MOR); then
    separating the biodiesel from the solid carbonaceous acid catalyst and the glycerol and/or other reaction byproducts, thereby obtaining the biodiesel.

2. The method of claim 1, further comprising
    pretreating the biodiesel feedstock to remove water, sulfur, phosphorous, phosphatides, gums, sterols, pigments, metals and/or dirt or other solid particles.

3. The method of claim 1, wherein the biodiesel feedstock comprises oil from bacteria, yeast, fungi, algae, or other microbes.

4. The method of claim 1, wherein the biodiesel feedstock comprises oil from marine algae.

5. The method of claim 1, wherein the alcohol is methanol.

6. The method of claim 1, wherein the solid carbonaceous acid catalyst has a BET surface area ranging from 2 to 3 $m^2/g$ and an acid site density of greater than 3.5 mmol/g.

7. A method for esterifying a biodiesel feedstock to produce biodiesel, comprising:
    contacting the biodiesel feedstock and at least one alcohol with a solid carbonaceous acid catalyst for a time and under conditions sufficient to produce biodiesel and glycerol,
    wherein the solid carbonaceous acid catalyst comprises carbonized and sulfonated biomass of lipid-extracted marine algae (BM); then
    separating the biodiesel from the solid carbonaceous acid catalyst and the glycerol and/or other reaction byproducts, thereby obtaining the biodiesel
    wherein the solid carbonaceous acid catalyst has a BET surface area ranging from about 15 to 25 $m^2/g$ and an acid site density of no more than 0.4 mmol/g.

8. The method of claim 1, wherein the separating the biodiesel comprises removing the solid carbonaceous catalyst, the alcohol, the glycerol, and water.

9. The method of claim 1, wherein solid carbonaceous acid catalyst is bound to a substrate and the contacting occurs in a fixed bed reactor.

* * * * *